(12) United States Patent
Maso Sabate et al.

(10) Patent No.: US 9,821,083 B2
(45) Date of Patent: Nov. 21, 2017

(54) VOLATILE SUBSTANCES EVAPORATION DEVICE

(71) Applicant: ZOBELE ESPANA, S.A., Barcelona (ES)

(72) Inventors: Jordi Maso Sabate, Barcelona (ES); Cedric Gobber, Barcelona (ES); Stefano Deflorian, Barcelona (ES)

(73) Assignee: ZOBELE ESPANA, S.A., Barcelona (ES)

( * ) Notice: Subject to any disclaimer, the term of this patent is extended or adjusted under 35 U.S.C. 154(b) by 19 days.

(21) Appl. No.: 14/889,761

(22) PCT Filed: Mar. 31, 2014

(86) PCT No.: PCT/ES2014/070244
§ 371 (c)(1),
(2) Date: Nov. 6, 2015

(87) PCT Pub. No.: WO2014/181015
PCT Pub. Date: Nov. 13, 2014

(65) Prior Publication Data
US 2016/0089467 A1    Mar. 31, 2016

(30) Foreign Application Priority Data
May 8, 2013    (ES) .................................. 201330664

(51) Int. Cl.
*A61L 9/03*    (2006.01)

(52) U.S. Cl.
CPC .............. *A61L 9/037* (2013.01); *A61L 9/03* (2013.01); *A61L 2209/133* (2013.01); *A61L 2209/135* (2013.01); *A61L 2209/15* (2013.01)

(58) Field of Classification Search
CPC ....................................................... A61L 9/037
(Continued)

(56) References Cited

U.S. PATENT DOCUMENTS

| | | |
|---|---|---|
| 2003/0138241 A1 | 7/2003 | Pedrotti et al. |
| 2006/0231544 A1* | 10/2006 | Zobele ............... A01M 1/2077 219/270 |
| 2008/0226269 A1 | 9/2008 | DeWitt et al. |

FOREIGN PATENT DOCUMENTS

| | | |
|---|---|---|
| EP | 0420144 A1 | 4/1991 |
| EP | 0 943 344 A1 | 9/1999 |

(Continued)

OTHER PUBLICATIONS

International Search Report from PCT/ES2014/070244, with an international filing date of Mar. 31, 2014, dated May 29, 2014, 7 pgs., Spanish Office of Patents and Trademarks, Madrid, Spain.

(Continued)

*Primary Examiner* — Kevin Joyner
*Assistant Examiner* — Holly Mull
(74) *Attorney, Agent, or Firm* — Baker & Hostetler LLP

(57) ABSTRACT

A volatile substances evaporation device comprises a body (1) which can house an element (2) impregnated with volatile substances; an electric resistance (4); and a plug (5) for connection to a power grid; and said electrical resistance (4) is positioned in said plug (5) and said plug (5) is movable with respect to said body (1) so that the distance between the element (2) and said electrical resistance (4) is variable, defining at least one position of maximum evaporation and one position of minimum evaporation.

5 Claims, 3 Drawing Sheets

(58) Field of Classification Search
USPC .......................................................... 422/125
See application file for complete search history.

(56)                    References Cited

FOREIGN PATENT DOCUMENTS

| EP | 0943344 A1 | 9/1999 |
|----|------------|--------|
| EP | 1386623 A1 | 2/2004 |
| EP | 1493210 A1 | 1/2005 |
| EP | 1 967 214 A1 | 9/2008 |
| ES | 2190143 T3 | 7/2003 |
| ES | 2 300 589 T3 | 3/2005 |
| JP | 037522 A | 1/1991 |
| WO | 9713539 A1 | 4/1997 |
| WO | 98/19526 A1 | 5/1998 |
| WO | 03/088430 A1 | 10/2003 |
| WO | 2004/002542 A1 | 1/2004 |
| WO | 2006/052519 A2 | 5/2006 |
| WO | 2006/124757 A2 | 11/2006 |

OTHER PUBLICATIONS

International Search Report and Written Opinion, from PCT/ES2014/070244 filed Mar. 31, 2014, issued May 29, 2014, 14 pgs, SPO, Madrid, Spain.
Search Report on the State of the Art, Application No. 201431891 filed Dec. 19, 2014, 7 pgs, SPO, Madrid, Spain.
European Patent Applicaton No. 14794512.5; Extended Search Report; dated Jan. 18, 2017; 7 pages.

\* cited by examiner

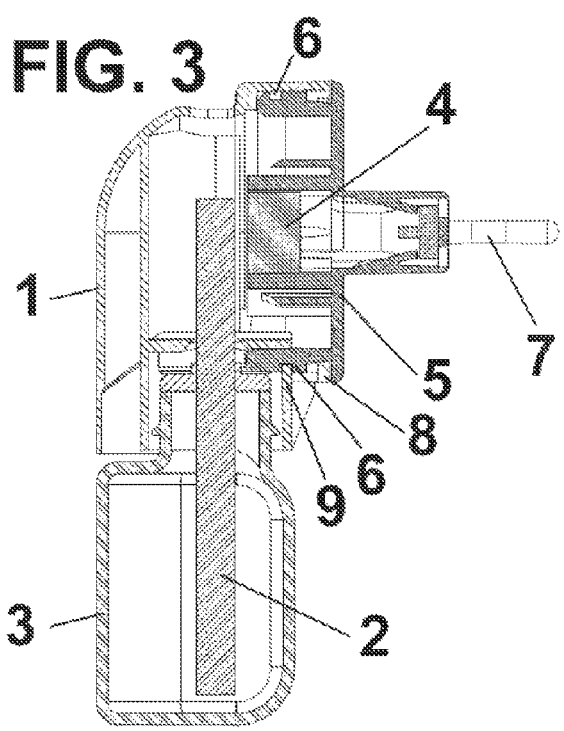

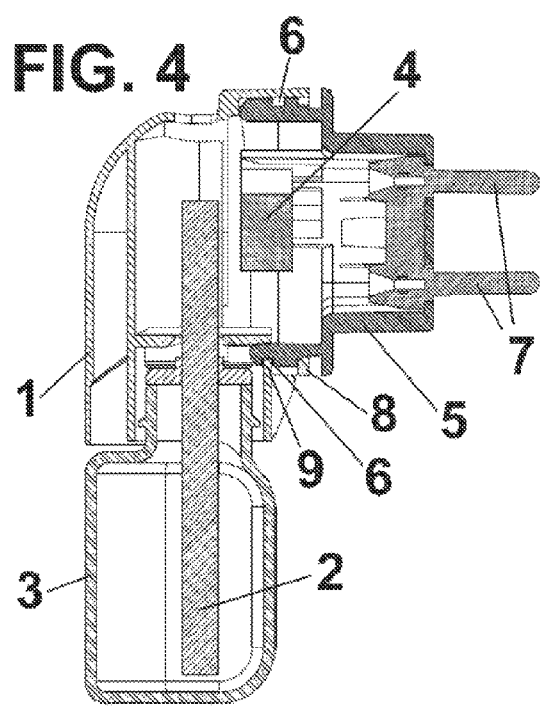

VOLATILE SUBSTANCES EVAPORATION DEVICE

CROSS-REFERENCE TO RELATED APPLICATIONS

The present application is a national stage entry of PCT/ES2014/070244, filed Mar. 31, 2014, which claims the benefit of Spanish Application Serial No. P201330664, filed May 8, 2013.

The present invention relates to a device for evaporating volatile substances, in particular an air freshener or an insecticide in which the evaporation of volatile substances is carried out by an electric resistance.

BACKGROUND OF THE INVENTION

Air fresheners or adjustable insecticides are known, where volatile substances are evaporated through an electrical resistance. In these air fresheners or adjustable insecticides, the regulation of the degree of evaporation is performed by rotating an additional component attached to the device.

This additional component for regulating evaporation has the disadvantage of adding complexity to the manufacturing process of the device and adds an extra cost to the final product.

EP 1967214 discloses a diffuser device for liquid substances, comprising a heating element and a porous element partially inserted in a tank. Said porous element may be positioned at an angle with respect to a plane (X) containing the plug, so that by varying said angle the evaporation of the liquid substance can be regulated. As indicated in the description, the diffuser allows a gradual and continuous adjustment of said evaporation.

U.S. Pat. No. 5,647,053 discloses a vapour delivery device comprising a heater block having a plug and a heating element, so that the block can rotate a predetermined amount around an axis parallel to the plug. The device also comprises a wick and an opening through the block. This block is rotatable 90° with respect to the rest of the device, but this rotation is not to regulate the evaporation, but to allow the vertical positioning of the housing, as indicated in the description.

WO 98/19526 discloses a device for the evaporation of chemical substances, comprising a wick associated with a bottle containing such chemical substances and a heating element, wherein the relative position of the wick and the heating element is adjustable. Regulating the evaporation is carried out by an arm, which can be positioned in different positions.

Therefore, an object of the present invention is to provide a volatile substance evaporation device that allows regulating the degree of evaporation without adding complexity to the device, so that its cost is reduced in comparison to known devices currently provided with regulation means.

In these known devices a gradual and continuous regulation is achieved, but not a minimum or maximum evaporation, defined by two different positions of the plug.

Therefore, an object of the present invention to provide a volatile substance evaporation device that allows the regulation of the degree of evaporation without adding complexity to the device, so that its cost is reduced in comparison to currently known devices provided with regulation means, and which can be used in any household, regardless of the orientation of the wall sockets.

DESCRIPTION OF THE INVENTION

With the volatile substance evaporation device of the invention the aforesaid disadvantages can be solved, presenting other advantages that will be described below.

The volatile substance evaporation device of the present invention comprises:
   a body that can house an element impregnated with volatile substances;
   an electrical resistance; and
   a plug for connection to a power grid;
and is characterised in that said electrical resistance is positioned in said plug and in that said plug is movable with respect to said body, so that the distance between said element and said electrical resistance is variable, defining at least one position of maximum evaporation and one position of minimal evaporation.

Advantageously, said plug is rotatable with respect to said body so that the rotation of said plug causes displacement of said electrical resistance with respect to said element impregnated with volatile substances.

According to a preferred embodiment, said electrical resistance is positioned in said plug and said plug is movable with respect to said body, so that the distance between said element and said electric resistance is maximal (minimum evaporation) when said plug is rotated 0° or 90° with respect to said body and the distance between said element and said electrical resistance is minimal (maximum evaporation) when said plug is rotated 180° or 270° with respect to said body.

Advantageously, this plug comprises a groove in which a projection from said body is housed, said groove comprising a first section closer to said body and a second section further away from said body, the first section of the groove covering approximately 90° and said second section of the groove also covering approximately 90°.

According to two alternative embodiments, said element is a wick impregnated with volatile substances from a reservoir, or said element is a tablet impregnated with volatile substances.

With the volatile substances evaporation device of the present invention a device with very simple adjustable evaporation with a reduced cost compared to other devices with adjustable evaporation is achieved, which requires no additional regulatory element, and which contains only two components: the body and the plug.

Furthermore, the volatile substance evaporation device of the present invention can be used with plug pins in which the orifices are arranged horizontally or vertically, allowing the placement of the device in its position of maximum or minimum evaporation in either case.

BRIEF DESCRIPTION OF THE DRAWINGS

For better understanding of what has been disclosed, drawings in which, schematically and solely by way of non-limiting example, a practical case of the embodiment is represented, are attached.

FIG. 3 is a sectional side view of the device of the present invention in its position of maximum evaporation; and FIG. 4 is a sectional side view of the device of the present invention in its position of minimum evaporation.

DETAILED DESCRIPTION OF A PREFERRED EMBODIMENT

Figure 1:
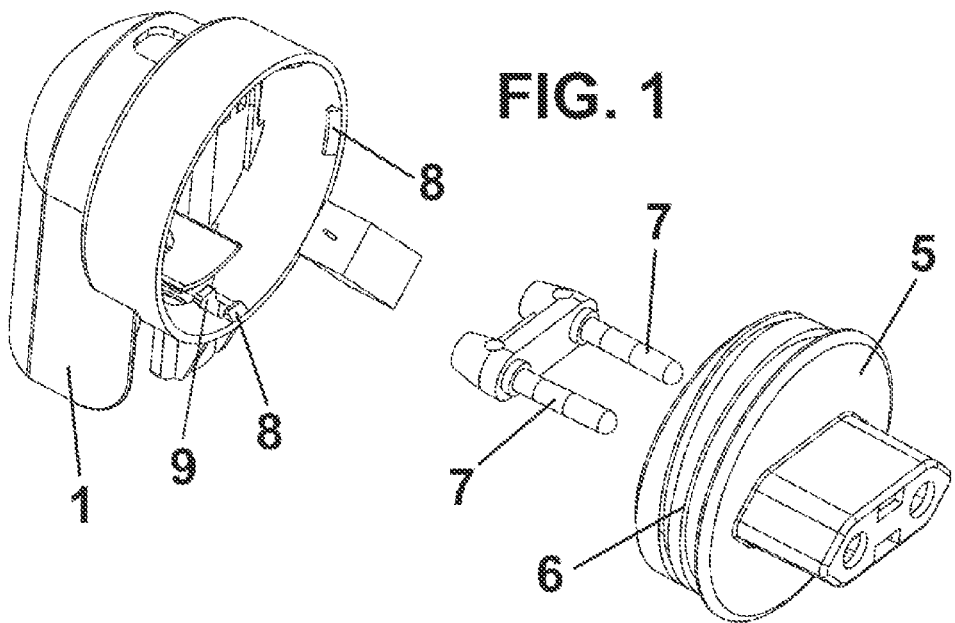
FIG. 1 is a perspective view of the device of the present invention with its components in an exploded view.
Figure 2:
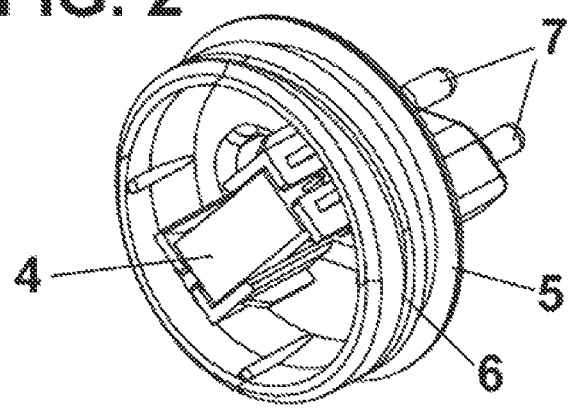
FIG. 2 is a perspective view of the plug of the device of the present invention from its rear.

The volatile substance evaporation device of the present invention consists of two components that are coupled together: a body 1 and a plug 5.

Said body 1 can house an element 2 which is impregnated with volatile substances, for example, a wick impregnated with volatile substances from a reservoir 3, which can be replaced when the volatile substances in its interior are exhausted. It is noted that said element impregnated with volatile substances could also be, for example, a tablet.

The plug 5 includes in its interior an electrical resistance 4 to heat said wick 2 and allow the evaporation of volatile substances impregnated therein. Furthermore, the plug 5 also comprises pins 7 for electrical connection, which can be placed in a horizontal position (FIG. 3) or in a vertical position (FIG. 4).

The coupling between the body 1 and the plug 5 is performed by a groove 6 provided in said plug 5, inside which a projection 9 of the body 1 is housed, allowing rotation of said plug 5 with respect to said body 1. Turning the plug 5 with respect to the body 1 produces a distancing or approaching movement of the plug 5 with respect to the body 1, so that the electrical resistance 4 also moves away from or closer to said impregnated element 2 (FIGS. 3 and 4). Also, the body 1 comprises stops 8 which contact said plug 5.

In FIG. 3, the position of maximum evaporation, i.e., the position where the electrical resistance 4 is closer to the impregnated element 2 is shown. In this position of maximum evaporation, said pins 7 of the plug 5 are in their horizontal position.

On the other hand, in FIG. 4, the minimum evaporation position, i.e., the position in which the electrical resistance 4 is further away from the impregnated element 2 is shown. In this minimum evaporation position, said pins 7 of the plug 5 are in their vertical position.

If the initial horizontal position of the pins 7 of the plug 5 is taken as reference, that is, a position of 0°, when the plug 5 is rotated 90° and the pins 7 are placed in their vertical position, the device is placed in its position of minimum evaporation. If the plug is rotated 90° more, to its position of 180°, the pins 7 are back in their horizontal position of maximum evaporation, and if it is rotated 90° more, in its position of 270°, the pins 7 are again in their vertical position of maximum evaporation.

This ability to place the evaporation device of the present invention in these four different positions is obtained thanks to the shape of the groove 6 of the plug 5. In particular, the groove 6 comprises a first section closer to said body 1 and a second section further away from said body 1, covering said first section of the groove 6 about 90°, and said second section of the groove 6 also covering about 90°.

As can be seen in FIGS. 3 and 4, in the position of maximum evaporation (FIG. 3), the projection 9 of the body 1 will be housed in said second section of the groove 6, whereas in the position of minimum evaporation (FIG. 4), the projection 9 of the body 1 will be housed in said first section of the groove 6.

Although reference has been made to a specific embodiment of the invention, it is apparent for a person skilled in the art that the volatile substances evaporation device described is susceptible to numerous variations and modifications, and that all the details mentioned can be replaced by others technically equivalent, without departing from the scope of protection defined by the appended claims.

The invention claimed is:

1. A volatile substances evaporation device, comprising:
   a body which can house an element impregnated with at least one volatile substance;
   an electric resistance;
   a plug for connection to a power grid;
      characterised in that said electrical resistance is positioned in said plug, wherein said plug is rotatable between at least 0° to 270° with respect to said body, so that the rotation of said plug causes movement of said electrical resistance with respect to said element impregnated with at least one volatile substance;
      further characterised in that the plug is rotatable to at least four positions:
         in a first position where the plug is at 0° with respect to said body and the distance between said element and said electrical resistance is maximal;
         in a second position where the plug is rotated to 90° with respect to said body and the distance between said element and said electrical resistance is maximal;
         in a third position where the plug is rotated to 180° with respect to said body and the distance between said element and said electrical resistance is minimal; and
         in a fourth position where the plug is rotated to 270° with respect to said body and the distance between said element and said electrical resistance is minimal.

2. The volatile substances evaporation device according to claim 1, wherein said plug comprises a groove in which a projection of said body is housed, said groove comprising a first section closer to said body and a second section further away from said body.

3. The volatile substances evaporation device according to claim 2, wherein said first section of the groove covers about 90° of the groove and said second section of the groove also covers about 90° of the groove.

4. The volatile substances evaporation device according to claim 1, wherein said element is a wick impregnated with at least one volatile substance from a reservoir.

5. The volatile substances evaporation device according to claim 1, wherein said element is a tablet impregnated with at least one volatile substance.

\* \* \* \* \*